United States Patent [19]
Hobbs et al.

[11] Patent Number: 5,916,154
[45] Date of Patent: Jun. 29, 1999

[54] METHOD OF ENHANCING PERFORMANCE IN PULSE OXIMETRY VIA ELECTRICAL STIMULATION

[75] Inventors: Steven E. Hobbs, Pleasanton; Ross Flewelling, Oakland, both of Calif.

[73] Assignee: Nellcor Puritan Bennett, Pleasanton, Calif.

[21] Appl. No.: 09/064,639

[22] Filed: Apr. 22, 1998

[51] Int. Cl.⁶ .................................................. A61B 5/00
[52] U.S. Cl. ........................... 600/334; 600/322; 600/473; 600/476
[58] Field of Search .................................. 600/310, 322, 600/323, 334, 335, 473, 476

[56] References Cited

U.S. PATENT DOCUMENTS

| | | |
|---|---|---|
| 4,211,222 | 7/1980 | Tapper . |
| 4,621,643 | 11/1986 | New, Jr. et al. . |
| 4,764,164 | 8/1988 | Sasaki . |
| 4,825,879 | 5/1989 | Tan et al. . |
| 4,926,867 | 5/1990 | Kanda et al. . |
| 4,928,691 | 5/1990 | Nicolson et al. . |
| 4,930,506 | 6/1990 | Ullrich . |
| 5,036,861 | 8/1991 | Sembrowich et al. . |
| 5,131,391 | 7/1992 | Sakai et al. . |
| 5,158,082 | 10/1992 | Jones . |
| 5,246,418 | 9/1993 | Haynes et al. . |
| 5,267,563 | 12/1993 | Swedlow et al. . |
| 5,279,543 | 1/1994 | Glikfeld et al. . |
| 5,392,777 | 2/1995 | Swedlow et al. . |
| 5,427,093 | 6/1995 | Ogawa et al. . |
| 5,547,467 | 8/1996 | Pliquett et al. . |
| 5,624,415 | 4/1997 | Cormier et al. . |
| 5,658,247 | 8/1997 | Henley . |
| B1 4,653,498 | 4/1989 | New, Jr. et al. . |

OTHER PUBLICATIONS

Telethermographhic Findings After Transcutaneous, (Massimo Leandri, Ottavia Brunetti & Carlo Parodi; Feb. 1986, pp. 210–213).

Pulsed Galvanic Stimulation: Efects of Current Frequency and Polarity on Blood Flow in Healthy Subjects (Bernice Hecker, MD, Harold Carron MD, David P. Schwardz, PhD; Arch Phys Med Rehabil vol. 66, Jun. 1985; pp. 369–371).

In Search of Mediators of Skin Vasoddilation induced by Transcutaneous Nerve timulation: III. Increase in Plasma VIP in Normal Subjects and in Raynaud's Dease (Birger Kaada, Egil Olsen and Olav Eielsen; Gen Pharmac. vol. 15, No. 2, pp. 107–113, 1984).

Medical Reflection Photometry (Dr. W.G. Zijlstra, Dr. G.A. Mook; VanGorcum's Medical Library nr. 152; 1962).

*Primary Examiner*—Cary O'Connor
*Assistant Examiner*—Eric F. Winakur
*Attorney, Agent, or Firm*—Hovey,Williams, Timmons & Collins

[57] ABSTRACT

An improved method for optically measuring a characteristic of a patient's blood or tissue is provided which involves first passing an arterialization current (typically from about 1–10 mA AC or DC) through a relatively short tissue segment of a patient (up to about 12 inches) for a period of time sufficient to significantly increase blood flow, whereupon a transcutaneous optical measurement is made. The method is especially suited for pulse oximetry and permits more accurate readings owing to the increased amplitude of the detection signal. In another embodiment, a probe molecule composition may be initially applied to the patient's skin, and the arterialization current is used to rapidly and evenly diffuse the probe molecule into the tissue segment. An appropriate sensor can then be employed for detecting the probe molecule.

16 Claims, 1 Drawing Sheet

METHOD OF ENHANCING PERFORMANCE IN PULSE OXIMETRY VIA ELECTRICAL STIMULATION

BACKGROUND OF THE INVENTION

1. Field of the Invention

The present invention is broadly concerned with a method for optically measuring a selected characteristic of a patient's blood or tissue by initially passing a current through a relatively short tissue segment of a patient in order to significantly increase blood flow therethrough, followed by transcutaneous illumination so as to develop information about a blood or tissue characteristic. Preferably, the invention is used in the context of pulse oximetry in order to generate a higher amplitude signal, thus giving more accurate results.

2. Description of the Prior Art

A common method of measuring blood gases (e.g., blood oxygen) involves taking a blood sample and examining it in a clinical blood gas analyzer. There are numerous drawbacks to this type of procedure. First, it is invasive and poses a risk of infection to the patient. Second, this method requires trained clinical personnel to sample and handle the potentially infectious blood. Finally, this approach provides only intermittent information about the blood components rather than continuous, up-to-the-minute measurements.

Non-invasive methods have been employed in order to avoid some of the above problems. One such method involves transcutaneous monitoring of physiological characteristics and components of the blood or tissue. In this technique, a portion of a patient's arterial blood-perfused tissue is transcutaneously illuminated and detected using light of two or more wavelengths. For example, changes in the amount of arterial blood in the tissue during a blood pressure pulse alters the amount and character of the light detected by the sensor's photodetector. The amounts of light transmitted through the tissue of each wavelength are then compared to calculate desired blood gas characteristics. In the case of pulse oximetry, this measurement determines to what degree the arterial blood flowing through the tissue is saturated with oxygen.

The quality of such measurements depends in part on the concentration of arterial blood in the portion of tissue illuminated by the sensor, and in part on the magnitude of the pulsatile changes in the amount of blood in the tissue. Accordingly, it is desirable to select advantageous sensor sites on the body known to have a high concentration of blood vessels (e.g., the fingers), or take other measures to insure a high blood flow concentration at the site. For example, prior practices have involved use of a chemical irritant applied topically at the sensor site to increase blood flow, with or without the application of heat. However, these expedients can cause excessive skin irritation when used for extended periods of time and thus are not practical for extended, continuous measurements. Furthermore, these effectively limit the choice of sensor sites, usually to the earlobes and fingertips.

Another prior approach for increasing arterial blood flow is embodied in the so-called "Cyclops" device used in the early 1960s. The Cyclops detects blood by measuring the amount of light reflected from the skin and is preferably placed in the middle of the forehead. The skin is first given a treatment using histamine phosphate, a counter irritant which has the effect of producing vascular dilation (when blood vessels are dilated, more blood will flow thus providing a larger signal to the sensor). A voltage is then applied to the skin to drive the histamine phosphate into the tissue by a process of iontophoresis. Subsequently, a compression plate is applied to the skin to render it bloodless and enable measurement of a baseline light reflection value. Thereafter, blood is allowed to flow to the dilated vessels, and measurements are taken of the blood oxygen level.

Despite all of these prior efforts, there remains a need in the art for an improved process which will enhance blood flow through tissue so as to increase the amplitude and strength of characterization signals, and especially pulse oximetry signals.

SUMMARY OF THE INVENTION

The present invention overcomes these problems and provides a simple method of generating increased blood flow through a segment of tissue of a patient so that blood gas or tissue characteristics may be more readily measured by transcutaneous illumination and detection. Moreover, the methods of the invention are non-invasive and minimize irritation to the patient's skin. Broadly speaking, an electric current is applied to the skin of a patient followed by transcutaneous illumination measurements, most commonly pulse oximetry. In another embodiment, improved measurements of physiological characteristics of blood or tissue are obtained by utilizing an electric current applied to the skin to provide rapid diffusion of probe molecules into the tissue, followed by optical detection of these probe molecules.

In more detail, two electrodes are placed on the skin of a subject at a selected sensor site, and a DC or AC current is applied to the electrodes. The electrodes can be positioned at varying distances apart, typically up to about 12 inches. While a conductant may or may not be applied to the skin prior to placing the electrodes, no therapeutic or pharmaceutical materials are applied to the skin or the electrodes, i.e., any material between the skin and electrode consists essentially of a conductant. While a variety of electrodes are suitable, the electrodes used in EKG monitoring are preferred. The electrodes can be placed on numerous sites on the patient's body, including the torso, wrist, and forehead.

Preferably, the applied current is from about 1 mA to about 10 mA, and most preferably from about 1–5 mA. The current can be applied for a period of from about 1–30 minutes, but preferably is applied for about 2–20 minutes. Advantageously, the current can be increased or decreased as necessary to maintain a desired pulse amplitude.

The current arterializes the tissue, causing tissue redness which is attributable to a vasodilation of the capillaries in the tissue. This arterialization leads to an increase in pulse amplitude, defined as the absolute or relative intensity of cardiac-induced modulation of light transmitted through tissue.

Improved measurement of arterial blood oxygen is carried out in accordance with the invention using a pulse oximeter after tissue arterialization and enhancement of blood flow from the application of current through the skin. It will be appreciated by one skilled in the art that measurement of arterial blood oxygen refers to measurement of the fraction of hemoglobin, that is oxygenated. An otherwise conventional pulse oximeter comprising a light source and a photodetector is positioned adjacent the arterialized tissue. Light is transmitted by the light source into the arterialized surface, and the photodetector detects differences in absorption and scattering between respective light wavelengths. Such transmittance and detection can be carried out only once or at regular intervals as determined by the user. Furthermore, the transmittance and detection can be carried out simultaneously with the application of current through the skin (after sufficient tissue arterialization has been achieved), or the operator can wait until the current is terminated.

While use can be made of separate electrodes and a pulse oximeter or similar device, it will be understood that all of the necessary equipment for carrying out the methods of the invention may be incorporated into a single device, i.e., a packaged apparatus for both delivery of the preliminary arterialization current, and transmission and detection of light.

In another embodiment, the arterialization current is used to rapidly drive a probe molecule into the tissue of a subject, and provides a predictable equilibrium of the probe molecule across the skin, resulting in more accurate determinations of blood components and physiological characteristics. This contrasts with prior practices by simply topically applying the probe and waiting for an indeterminate time for passive diffusion thereof through the skin. In one embodiment of the present invention, a composition (usually a liquid or gel) is initially applied to the skin at the sensor site separately or with the conductant so that any material between the electrodes and skin consists essentially of the conductant and probe. In a second embodiment, the probe can be included in the electrode. In either embodiment, a conductant may or may not be applied to the skin prior to attaching the electrodes. This is followed by application of arterialization current as described previously, using the same ranges of current and time. Thereafter, an appropriate sensor such as a fluorimetric sensor, spectrophotometric sensor or pulse oximeter is used to non-invasively measure the desired characteristic based upon the probe molecule's effect on the light transmitted into the skin. By selecting a suitable probe and sensor, monitoring for characteristics such as amounts of blood/tissue $O_2$, $CO_2$, pH, lactate, or electrolyte levels such as $Na^+$, $Ca^{2+}$ and $K^+$ can be made.

One exemplary probe molecule is quinine which has a fluorescence lifetime depending upon the oxygen pressure in the tissue. When quinine is diffused into a target tissue segment, the fluorescence lifetime thereof allows determination of oxygen pressure in the tissue. Another exemplary probe would be a pH sensitive dye whose color, measured optically, indicate tissue pH. Clearly, a variety of probes can be used in the context of the invention, some of which are set forth in the following table.

TABLE

Exemplary Probe Molecules[1]

| pH Fluorescent Probes | pH Absorbance Probes | Fluorescent $Ca^{2+}$ Probes | Fluorescent Oxygen Probes |
|---|---|---|---|
| fluorescein | cresol red | fura red | metalloporphyrins |
| BCECF[2] | bromothymol blue | calcium green | quinine |
| SNAFL[3] | | | ruthenium complexes osmium complexes |

[1]Typically dispersed in compatible solvents at a concentration of from about 0.5–1.5 μM.
[2]BCECF - 2',7'-bis-(2-carboxyethyl)-5-carboxyfluorescein
[3]SNAFL - seminaphthofluoresceins It will be appreciated that this invention provides a simple and effective method for enhancing the detectable optical signal obtained in a variety of non-invasive transcutaneous illumination assays. Although the methods hereof can be used on any patient, they are particularly beneficial for monitoring infants at risk for hypoxemia during sleep (e.g., Sudden Infant Death Syndrome) and patients who require the assistance of mechanical ventilation for survival.

DETAILED DESCRIPTION OF THE PREFERRED EMBODIMENT

Figure 1:
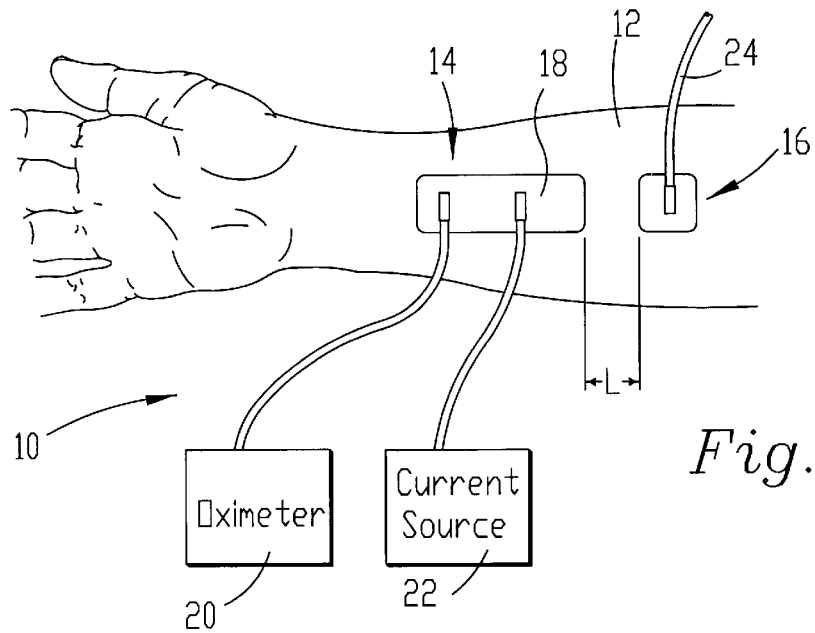
FIG. 1 is a schematic illustration of one exemplary apparatus useful in carrying out the methods of the present invention.

Turning to the drawing, FIG. 1 illustrates an apparatus 10 in accordance with the invention, applied to the forearm 12 of a patient. The apparatus 10 includes a combined oximeter/current source 14 and a second electrode 16. The oximeter/current source 14 has a pad 18 with oximeter 20 and current source 22 operatively coupled thereto. As will be readily appreciated, the pad 18 serves in part as a first electrode for the overall apparatus 10. The second electrode 16 is likewise of conventional design and has a lead 24 operatively connected to the electrical circuitry of the source 22. It will be observed that the second electrode 16 is spaced a distance L from the electrode of pad 18.

It will be appreciated that many variations can be made in the apparatus 10 within the ambit of the invention. Thus, a packaged device can be readily manufactured having a pair of spaced electrodes and an oximeter operatively coupled to a single skin-engaging pad. Also, other types of detectors as described above can be used in lieu of the oximeter 20.

The following example sets forth one technique useful for carrying out the methods of the present invention. It is to be understood that this example is presented by way of illustration only, and nothing therein should be taken as a limitation upon the overall scope of the invention.

EXAMPLE

Pulse oximetry measurements were made using a Nellcor Puritan Bennett (NPB) N3000 pulse oximeter set up as illustrated in FIG. 1. The oximeter included an NPB RS-10 sensor pad 18 having tin-plated copper mesh attached to the sensor surface to serve as an electrode (not shown). A clear, conductive gel pad (Clear Tac Part # CT18) was placed on the copper mesh. The RS-10 sensor pad 18 and a 20×38 mm infant pediatric ECG electrode 16 were placed on the inside forearm 12 of a Caucasian subject. The sensor pad 18 and the electrode 16 were positioned approximately 1.5 inches apart. No therapeutic or other preparations were applied to either the patient's skin or the sensor pad 18 or electrode 16.

A 2.0 mA DC current was applied via current source 22 through the electrode of sensor pad 18 for 15 minutes. The electrode 16 and sensor pad 18 were then removed, and the tissue segment under the electrode and sensor was observed to be bright red. The redness slowly decreased over the period of 30 minutes to 1 hour after the current was terminated.

Figure 2:
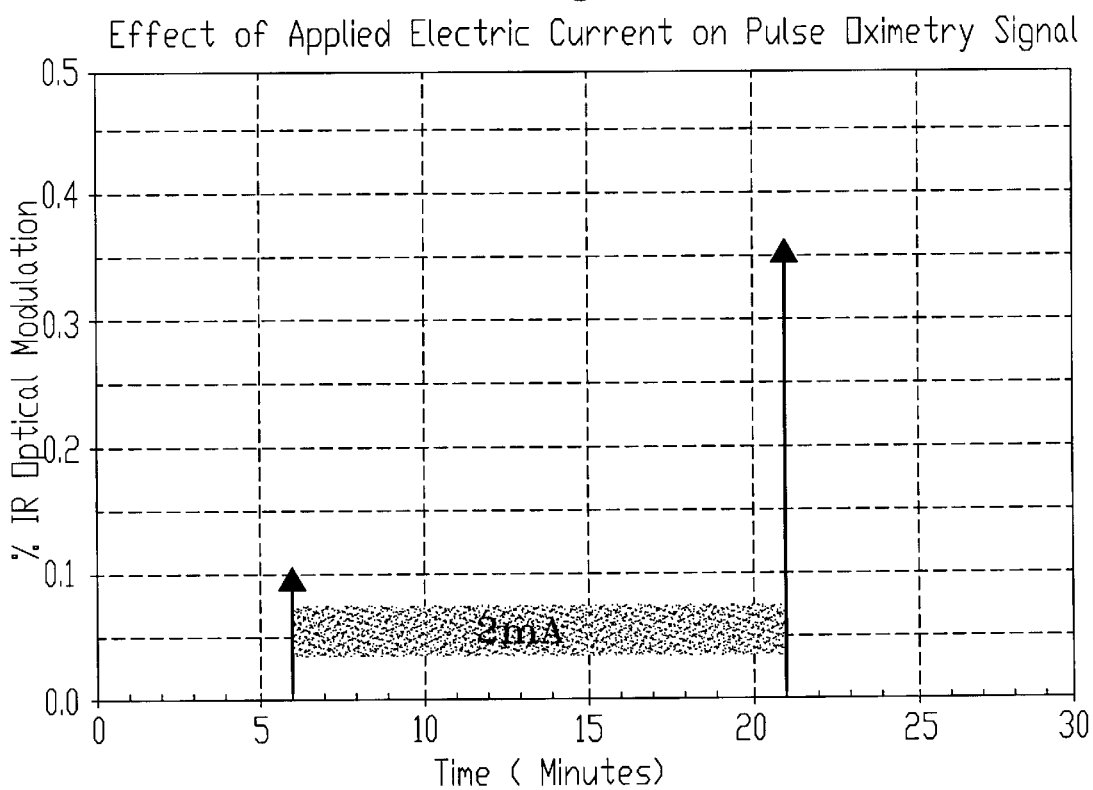
FIG. 2 is a graph demonstrating the enhanced signal achieved in a pulse oximetry experiment using preliminary arterialization current.

The change in perfusion was measured by observing the optical modulation of the pulse oximetry signal before, during, and after the current was applied. As shown in FIG. 2, the modulation before applying the current to the electrodes was approximately 0.10%. The modulation continued to increase as the current was applied and reached approximately 0.35% when the current was reduced to zero. Thus, a threefold increase in optical modulation of the pulse oximetry signal was obtained due to the application of the DC current to the tissue. Similar increases in optical modulation were observed for low frequency (<0.3 Hz) AC current.

We claim:

1. A method of optically measuring a characteristic of a patient's blood or tissue comprising the steps of:

(a) passing a current through a tissue segment of a patient, the tissue segment having blood flow therethrough, including the steps of placing a pair of electrodes on the patient's skin at a distance apart of up to about twelve inches, and passing the current through the electrodes and the tissue segment therebetween in order to increase the blood flow through the tissue segment without the use of chemical irritants or perfusion enhancing solutions;

(b) transmitting light into a test site in the tissue segment during the time of the increased blood flow; and (c) detecting light adjacent the test site as a parameter indicative of the characteristic to be measured.

2. The method of claim 1, said characteristic to be measured being the amount of arterial blood oxygen.

3. The method of claim 1, wherein the current is from about 1 mA to about 10 mA.

4. The method of claim 1, wherein the steps of transmitting and detecting are performed with a pulse oximeter.

5. The method of claim 4, further including the step of varying the current to maintain an enhanced signal from the pulse oximeter.

6. The method of claim 1, wherein the current is applied for about 1 minute to about 30 minutes.

7. The method of claim 1, further including the steps of applying a composition containing a probe molecule to a portion of the patient's skin adjacent said tissue segment prior to said current passing step, and causing said probe molecule to be transmitted through the patient's skin by said passage of current.

8. The method of claim 7, said probe molecule being selected from the group consisting of pH fluorescent probes, pH absorbance probes, fluorescent $Ca^{2+}$ probes and fluorescent oxygen probes.

9. The method of claim 1, wherein said characteristic to be measured is the amount of a selected gas in the patient's blood.

10. The method of claim 9, wherein the gas is selected from the group consisting of oxygen and carbon dioxide.

11. The method of claim 1, wherein said characteristics to be measured is the amount of an electrolyte in the patient's blood.

12. The method of claim 11, wherein the electrolyte is selected from the group consisting of $Na^+$, $Ca^{2+}$, and $K^+$.

13. The method of claim 1, wherein said characteristics to be measured is tissue oxygen pressure.

14. The method of claim 1, wherein said characteristic to be measured is pH.

15. The method of claim 1, one of said electrodes including a pad and further including the steps of applying a probe molecule to said electrode pad prior to said current passing step, and causing said probe molecule to be transmitted through the patient's skin by said passage of current.

16. The method of claim 15, said molecule being selected from the group consisting of pH fluorescent probes, pH absorbance probes, fluorescent $Ca^{2+}$ probes and fluorescent oxygen probes.

* * * * *